(12) United States Patent
Portman

(10) Patent No.: US 6,468,962 B1
(45) Date of Patent: Oct. 22, 2002

(54) NUTRITIONAL INTERVENTION COMPOSITION FOR ENHANCING AND EXTENDING SATIETY

(75) Inventor: Robert Portman, Woodbridge, NJ (US)

(73) Assignee: Pacific Health Laboratories, Inc., Woodbridge, NJ (US)

( * ) Notice: Subject to any disclaimer, the term of this patent is extended or adjusted under 35 U.S.C. 154(b) by 18 days.

(21) Appl. No.: 09/745,516

(22) Filed: Dec. 22, 2000

Related U.S. Application Data (62) Division of application No. 09/510,809, filed on Feb. 23, 2000, now Pat. No. 6,207,638.

(51) Int. Cl.$^7$ ................................................ A01N 37/18
(52) U.S. Cl. ........................... 514/2; 514/773; 514/775; 514/780; 514/783
(58) Field of Search ............................. 514/2, 773, 775, 514/777, 780, 782, 783; 424/195.1, 725; 426/233, 324, 524, 658, 801, 72, 74

(56) References Cited

U.S. PATENT DOCUMENTS

| | | |
|---|---|---|
| 4,491,578 A | 1/1985 | Peikin |
| 4,833,128 A | 5/1989 | Solomon et al. |
| 4,970,207 A | 11/1990 | Sato et al. |
| 5,086,042 A | 2/1992 | Rosamond |
| 5,187,154 A | 2/1993 | Phillips et al. |
| 5,314,886 A | 5/1994 | Becker et al. |
| 5,382,664 A | 1/1995 | Sato et al. |
| 5,470,839 A | 11/1995 | Laughlin et al. |
| 5,556,969 A | 9/1996 | Chambers et al. |
| 5,609,904 A | 3/1997 | Koh et al. |
| 5,674,896 A | 10/1997 | Yoshida et al. |
| 5,703,052 A | 12/1997 | Deninno et al. |
| 5,750,353 A | 5/1998 | Kopin et al. |
| 5,814,316 A | 9/1998 | Cook et al. |
| 5,827,517 A | 10/1998 | Cook et al. |
| 5,932,561 A | 8/1999 | Meyers et al. |
| 5,989,584 A | 11/1999 | Cook et al. |
| 6,039,985 A | 3/2000 | Kamarei |

FOREIGN PATENT DOCUMENTS

WO    WO0022937    4/2000

Primary Examiner—Jon P. Weber
Assistant Examiner—Patricia Patten
(74) Attorney, Agent, or Firm—Gibbons, Del Deo, Dolan, Griffinger & Vecchione

(57) ABSTRACT

The invention relates to a nutritional intervention composition that enhances and extends satiety in a calorically efficient manner. In particular, the invention contains protein, long chain fatty acids, calcium, soluble and insoluble fibers to stimulate CCK and prevent its subsequent inactivation and inhibition. By stimulating CCK and extending satiety the method is useful for the treatment of overweight individuals, individuals with Type II diabetes and individuals with bulimia.

11 Claims, 10 Drawing Sheets

FIGURE 1

Effect of Nutritional Intervention Composition on Hunger Ratings over Time Compared to Placebo

FIGURE 2

Effect of Nutritional Intervention Composition on Food Consumption Ratings over Time Compared to Placebo

FIGURE 3

Effect of Nutritional Intervention Composition or Placebo Added to Yogurt on Hunger Ratings over Time Compared to Placebo

Effect of Nutritional Intervention Composition or Placebo Added to Yogurt on Change in Hunger Ratings over Time Compared to Placebo

FIGURE 5

Effect of Nutritional Intervention Composition Added to Yogurt on Food Consumption Ratings over Time Compared to Placebo

FIGURE 6

Effect of Nutritional Intervention Composition on Appetite Change over 6 Weeks

FIGURE 7

Effect of Nutritional Intervention Composition on Food Cravings over 6 Weeks

FIGURE 8

Effect of Nutritional Intervention Composition on Appetite over 6 Weeks

FIGURE 9

Effect of Nutritional Intervention Composition on Weight Loss over 6 Weeks

FIGURE 10

Effect of Nutritional Intervention Composition on Satiety Ratings over 6 Weeks

|  | Test Group | | | | | | |
|---|---|---|---|---|---|---|---|
|  | Before | Week 1 | Week 2 | Week 3 | Week 4 | Week 5 | Week 6 |
| Base: Total completers | (113) A | (113) | (113) | (113) | (113) | (113) | (113) B |
| I have experienced changes in my appetite | 3.3 | 2.7 | 2.6 | 2.4 | 2.5 | 2.4 | 2.6 |
| I crave food all the time | 3.2 | 3.7 | 3.5 | 3.6 | 3.6 | 3.8 | 3.7 |
| I have no appetite at all | 4.4 | 3.9 | 3.9 | 3.8 | 3.8 | 3.7 | 3.8 |

NUTRITIONAL INTERVENTION COMPOSITION FOR ENHANCING AND EXTENDING SATIETY

This application is a Divisional of application Ser. No. 09/510,809 filed Feb. 23, 2000, now U.S. Pat. No. 6,207,638.

FIELD OF THE INVENTION

The present invention relates to a nutritional intervention composition for enhancing satiety prior to the consumption of a meal resulting in reduced caloric intake during the meal, and lengthening the inter-meal interval by extending satiety for up to three hours following the meal. More particularly, the nutritional intervention composition includes a protein source, long chain fatty acids, and calcium to stimulate the release of cholecystokinin (CCK). Further, the nutritional composition includes soluble and insoluble fibers to bind bile acids and bile salts that inhibit the release of CCK. By extending the feeling of satiety, the nutritional intervention composition decreases food intake producing weight loss over time. The composition can be taken prior to a meal or can be mixed with food to extend the satiation effect of that food.

The present invention also relates to a nutritional intervention composition to help individuals with Type II diabetes maintain glycemic control and extend satiety. By extending the feeling of satiety, the nutritional intervention composition decreases food intake resulting in a decrease in body weight over time while providing better regulation of glucose and insulin levels following consumption of a meal. Furthermore, since CCK causes a delay in stomach emptying, the nutritional intervention composition can slow the absorption of glucose by the small intestine further improving glycemic control.

The present invention also relates to a nutritional intervention composition designed as an adjunct to treat patients with bulimia and eating disorders who have been shown to have a defect in their satiety control mechanisms. By stimulating satiety before a meal and extending satiety after a meal, the present invention reduces binge eating in bulimic patients.

BACKGROUND OF THE INVENTION

Satiety

Cholecystokinin (CCK) is a peptide released following the consumption of food. The literature demonstrates an injection of CCK in animals elicited the total range of satiety behavior. When injected CCK levels peak quickly and usually return to baseline with an hour. The drop in CCK levels is associated with a decline in the characteristic satiety behavior.

Release of cholecystokinin has also been shown to be a satiety signal in humans. In 1981, researchers showed that an injection of CCK decreased food intake by 16 percent. The subjects did not alter their rate of eating but rather stopped eating earlier, which would be the expected results if cholecystokinin were a satiety signal. The results in humans confirmed the results in the laboratory that CCK is an important agent in terminating the meal. CCK levels in man peak within 20 minutes following a meal and usually returns to baseline in one hour. Although the full mechanism whereby CCK exerts its effect on satiety is not known, there appears to be two components, a central component involving CCK receptors in the brain and a peripheral component involving the stomach and small intestine.

When food is consumed, CCK releasing protein (CCKRP) is released in the small intestine. CCKRP stimulates CCK release from intestinal cells. The release of CCK generates the behavioral symptoms associated with satiety and at the same time activates a number of negative feedback mechanisms to turn off the CCK response. There are primarily two negative feedback mechanisms, one involving proteases secreted by the pancreas and the second bile from the gallbladder. CCK stimulates the pancreas to secrete a number of proteases, specifically trypsin and chymotrypsin, which inactivate CCKRP. CCK also stimulates gallbladder contraction causing bile acids to be released into the intestinal lumen. Bile acids are powerful regulators of CCK, inhibiting its release.

The literature has also shown that CCK release can be stimulated by protein such as whey and casein, hydrolysis products of casein including glycomacropeptide, phenylalanine, calcium and long chain fatty acids. All of the literature to date has shown that regardless of how CCK is stimulated or what intervention is taken to prevent its breakdown, its reported effect is on the termination of the meal.

It has been well documented that some soluble and insoluble fibers as well as plant saponins bind bile salts. In fact, it is the binding of bile salts by fiber, which is believed partly responsible for the hypocholestrolemic effect of these agents. Different fibers have different binding capacities to the various bile acids and salts. For instance, cellulose has been shown to bind bile acids poorly.

The ability of CCK to reduce appetite would appear to make it an extremely useful agent in treating obesity. In a weight management program, stimulation of CCK would result in less food consumed and reduction of hunger cravings between meals. These effects would enable an overweight individual to better comply with a diet that has a reduced caloric intake. The major limitation in the use of CCK, as an appetite control agent, is that it must be given by injection. Additionally, CCK release initiates a number of negative feedback mechanisms described above involving the pancreas and gallbladder that terminate the CCK response.

There is a definite need in the art for a nutritional intervention composition that can be taken orally to permit a subject to be satiated with a lower caloric intake. There is also a definite need in the art for a nutritional intervention composition that not only can be taken prior to a meal to stimulate satiety before the meal but whose properties extend satiety following the meal thereby lengthening the inter-meal interval.

There is also a definite need in the art for a nutritional intervention composition that can be taken orally and that with a total caloric value of only 80 calories can strongly provoke satiety.

Glycemic Control

It is well known the art that slowing gastric emptying can blunt the post-prandial rise in glucose and insulin. Most persons with Type II diabetes are obese and have an inability to respond normally to insulin. Obesity is a major contributing factor to the development of Type II diabetes. The primary treatment for Type II diabetics is diet and a weight loss program. Dietary guidelines for Type II diabetics include consumption of fiber. Fiber has been shown to slow gastric emptying. One of the prominent effects of cholecystokinin is also to delay gastric emptying. The ability of fiber and cholecystokinin to delay gastric emptying are well known in the art and the result of delayed gastric emptying is to slow the absorption of glucose.

There is a definite need in the art for a nutritional intervention composition that can be taken orally by Type II diabetics that stimulates the release of CCK in a calorically efficient way, and that permits Type II diabetics to be satiated with a lower caloric intake and offers a better degree of glycemic control.

There is a definite need in the art for a nutritional intervention composition that not only can be taken prior to a meal to stimulate satiety before the meal but whose properties extend satiety following the meal thereby lengthening the intermeal interval in order to help the Type II diabetic lose weight.

Bulimia

Bulimia is an eating disorder that usually effects females. A major characteristic of bulimia is an inability to become satiated by food. As a result bulimics tend to binge on food and regurgitate it to prevent weight gain. This disorder is classically treated with psychotherapy. Studies have shown that bulimics have a defect in their normal satiety mechanisms. They release less CCK following a meal.

There is a definite need in the art for a nutritional intervention composition that can be taken orally by bulimics, and is a calorically efficient stimulator of CCK to permit bulimics to be satiated. An important element of this invention is the design of a product that not only can be taken prior to a meal to stimulate satiety before the meal but whose properties extend satiety following the meal thereby lengthening the inter-meal interval.

DESCRIPTION OF THE PRIOR ART

Satiety

U.S. Pat. No. 4,833,128 discloses the oral administration of phenylalanine in conjunction with protein, carbohydrate and fat to stimulate satiety. This invention teaches that when a dietary supplement containing phenylalanine is consumed fifteen minutes prior to a meal, it generates a feeling of satiety resulting in less food consumption at the subsequent meal. The CCK release slows gastric emptying and the fiber in the invention provides an additional effect by slowing gastric emptying. The nutritional supplement in this patent contains 140 calories and it is recommended that it be taken three times a day. At a dose of three times a day this dietary supplement would provide almost 25% of the total calories suggested in a reduced caloric program (1600 calories) to lose weight. Furthermore, the addition of phenylalanine limits its use in patients with phenylketonuria. The invention also teaches that cellulose should be added. Cellulose has been shown to be one of the poorest binders of bile acids and therefore would not stimulate satiety by blocking the effect of bile acids and salts on cholecystokinin release. Finally, the invention does not have any effect on extending the duration of action of CCK. In fact, the invention teaches that the appetite suppression of CCK may be merely temporary resulting in a limited satiety effect.

U.S. Pat. No. 4,491,578 discloses the oral administration of a trypsin inhibitor to enhance satiety by stimulating the release of CCK. This patent teaches that the negative feedback signal for cholecystokinin secretion results from the release of trypsin from the pancreas. The administration of a therapeutically effective quantity of trypsin inhibitor blocks the trypsin released from the pancreas thereby interfering with a negative feedback mechanism. The nutritional intervention composition described in this application does not depend on trypsin inhibition for its effect on satiety.

U.S. Pat. No. 5,932,561 teaches that dietary supplements that bind lipids can aid in weight loss and reduce cholesterol. The patent also teaches that a dietary supplement composition that contains saponins from aloe increase the capacity of chitosan to bind fat. The saponins also act as a laxative to off set the constipating effects of chitosan. This patent does not teach that either chitosan or saponins can be used to stimulate cholecystokinin. The weight management characteristics of this invention are to primarily combine fat and cholesterol and remove it from the body.

U.S. Pat. No. 5,703,052 teaches that saponins are useful in controlling hypercholesterolemia. This patent does not describe the use of saponins as a stimulator of CCK.

Glycemic Control

U.S. Pat. No. 5,187,154 teaches that Type II diabetics exhibit more rapid gastric emptying than normal controls in the early stages of their diagnosis and that an invention that can slow gastric emptying will improve glycemic control. The patent also teaches that the invention is useful for assessing the risk of diabetes in subjects who do not show any abnormalities in glucose metabolism. The patent utilizes a therapeutic dose of trypsin inhibitor to stimulate CCK release and thereby slow gastric emptying which in turn results in improved glycemic control. The nutritional intervention described in the present invention does not depend on trypsin inhibition for its effect on glycemic control.

None of the prior art patents disclose the nutritional composition of the present invention for enhancing and extending satiety with a calorically efficient preparation.

OBJECTS

Accordingly it is an object of the present invention to provide a nutrition intervention composition for enhancing satiety before a meal.

Another object of the present invention is to provide a nutrition intervention composition to extend satiety after a meal.

Another object of the present invention is to provide a nutrition intervention composition that can be consumed prior to a meal to enhance satiety.

Another object of the present invention is to provide a nutrition intervention composition that can be added to food to extend the satiating effect of the food to which. it is added.

Another object of the present invention is to provide a nutrition intervention composition to stimulate cholecystokinin release in a calorically efficient manner.

Another object of the present invention is to provide a nutrition intervention composition to increase cholecystokinin by stimulating its release through a combination of nutritional agents.

Another object of the present invention is to provide a nutrition intervention composition to stimulate cholecystokinin release by binding to bile acids and to bile salts.

Another object of the present invention is to provide a nutrition intervention composition to cause weight loss resulting from a reduced caloric intake.

Another object of the present invention is to provide a nutrition intervention composition to provide better glycemic control for Type II diabetics.

Another object of the present invention is to provide a nutrition intervention composition to help Type II diabetics enhance and extend satiety in a calorically efficient fashion.

Another object of the present invention is to provide a nutrition intervention composition to increase satiety in bulimics who have a defect in their normal CCK release mechanism.

Another object of the present invention is to provide a nutrition intervention composition to help in the management of the bulimic patients.

Another object of the present invention is to provide a nutrition intervention composition that is palatable, well tolerated and without side effects to individuals.

SUMMARY OF THE INVENTION

In brief this invention relates to a nutritional intervention composition in a dry powder form for enhancing satiety prior to a meal and extending satiety after a meal in a calorically efficient fashion. The dry nutritional composition includes protein, casein, glycomacropeptide, long chain fatty acids, calcium, and soluble and insoluble fibers.

The dry nutritional composition includes protein in the range of 5.56% to 46.89%.

The dry nutritional composition further includes a glycomacropeptide in the range of 0.15% to 15.38%. The dry nutritional composition also includes oleic acid in the range of 5.56% to 46.89% and other long chain fatty acids in the range of 11.11% to 58.62%. The dry nutritional composition also includes soluble fiber in the range of 5.56% to 46.89%. In addition, the soluble fiber serves as a source of plant saponins. The dry nutritional composition also includes insoluble fiber in the range of 2.70% to 37.36%.

The dry nutritional composition may be mixed with water or other liquids to form a drink. Also, it can be added to food.

BRIEF DESCRIPTION OF THE DRAWINGS

Further objects, features, and advantages of the present invention will become apparent upon the consideration of the following detailed description of the presently preferred embodiment when taken in conjunction with the accompanying drawings, wherein.

DETAILED DESCRIPTION OF THE INVENTION

Figure 1:
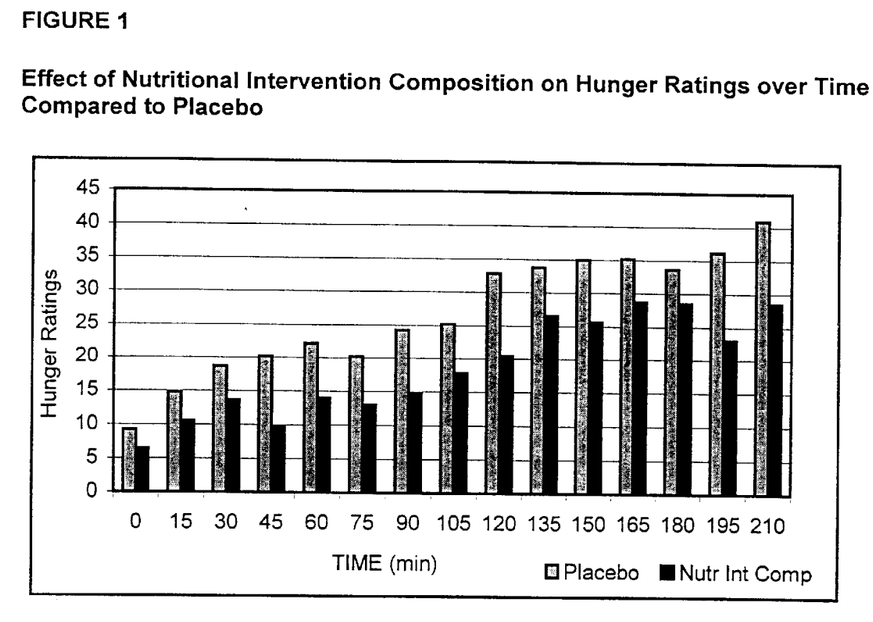
FIG. 1 is a graph showing a comparison of hunger ratings between a placebo group and the nutritional intervention composition of the present invention.
Figure 2:
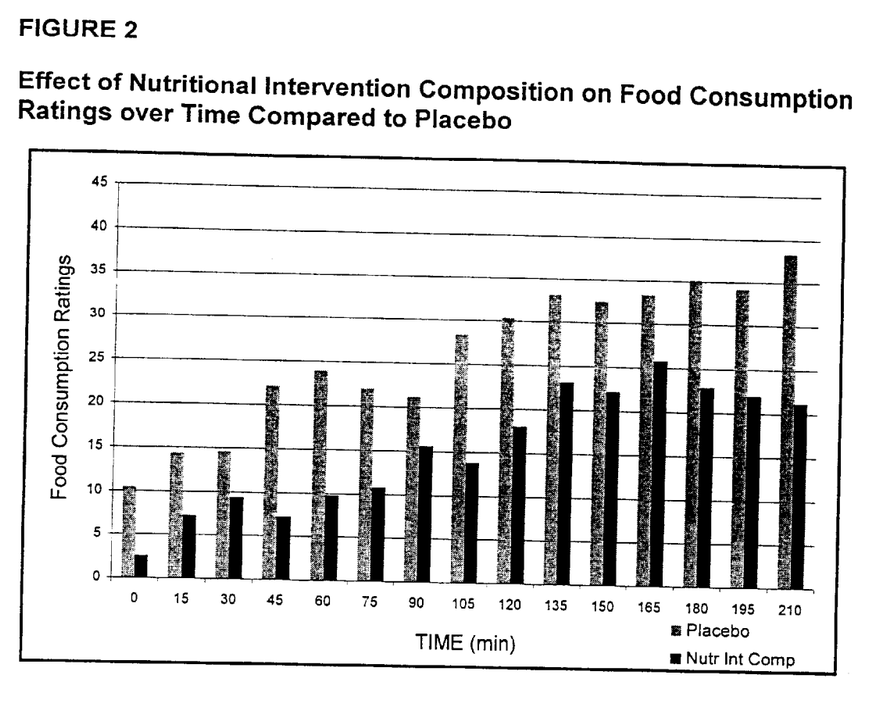
FIG. 2 is a graph showing a comparison of food consumption ratings between a placebo group and the nutritional intervention composition of the present invention.
Figure 3:
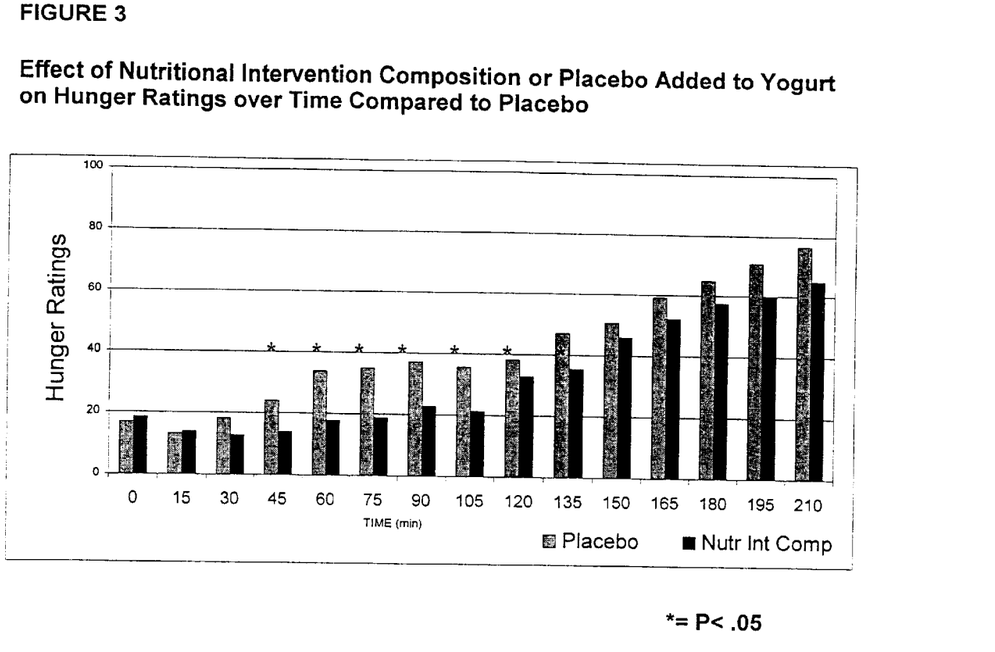
FIG. 3 is a graph showing a comparison of hunger ratings following consumption of two forms of low fat yogurt, one containing a placebo mixture and the other containing the nutritional intervention composition of the present invention.
Figure 4:
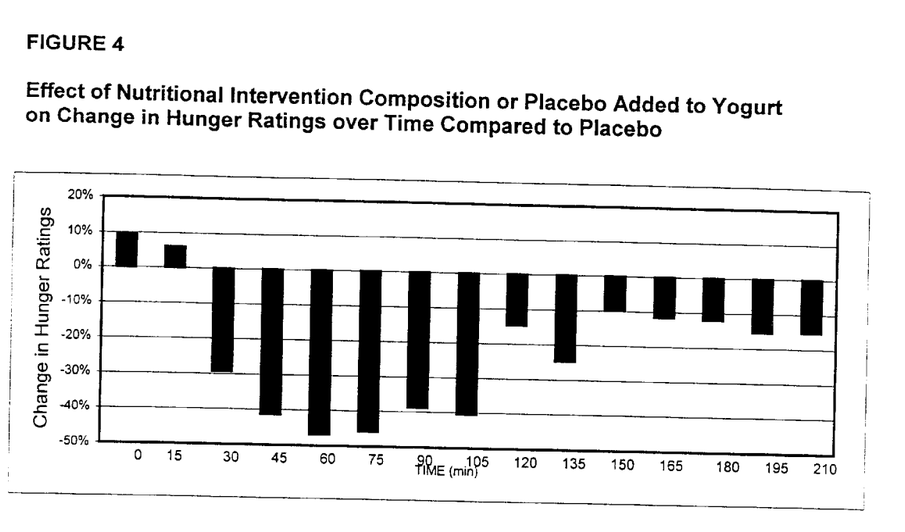
FIG. 4 is a graph showing a comparison of the change in hunger ratings over time following consumption of two forms of low fat yogurt, one containing a placebo mixture and the other containing the nutritional intervention composition of the present invention.
Figure 5:
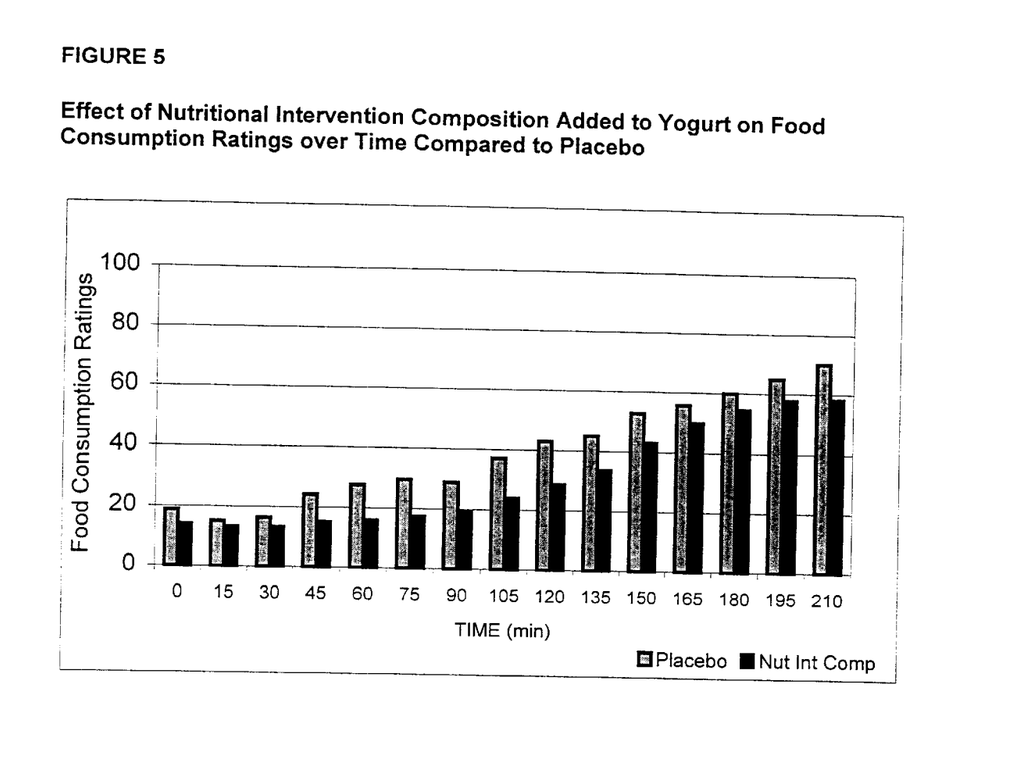
FIG. 5 is a graph showing a comparison of food consumption ratings following consumption of two forms of low fat yogurt, one containing a placebo mixture and the other containing the nutritional intervention composition of the present invention.
Figure 6:
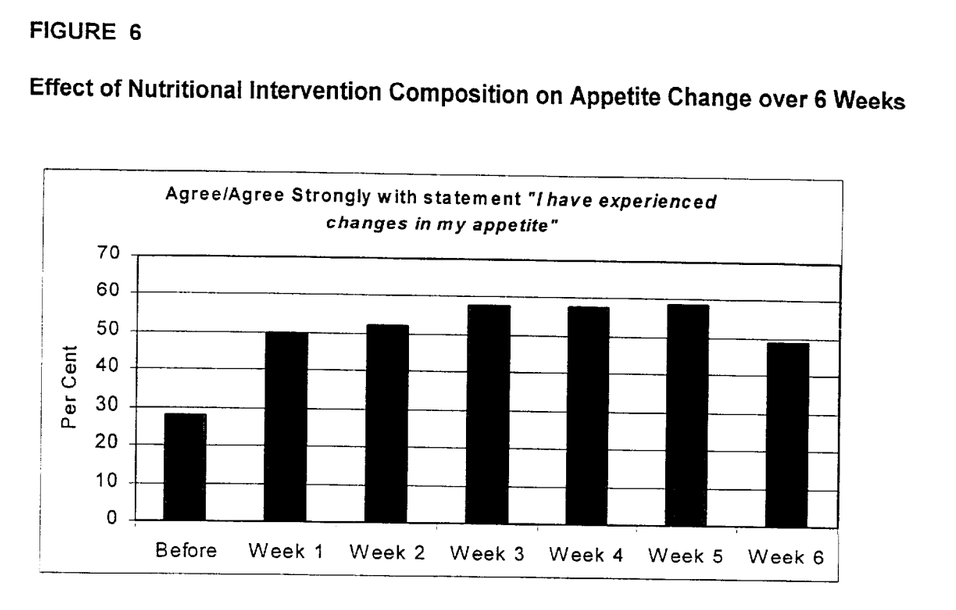
FIG. 6 is a graph showing the effect of the nutritional intervention composition on appetite change over six weeks.
Figure 7:
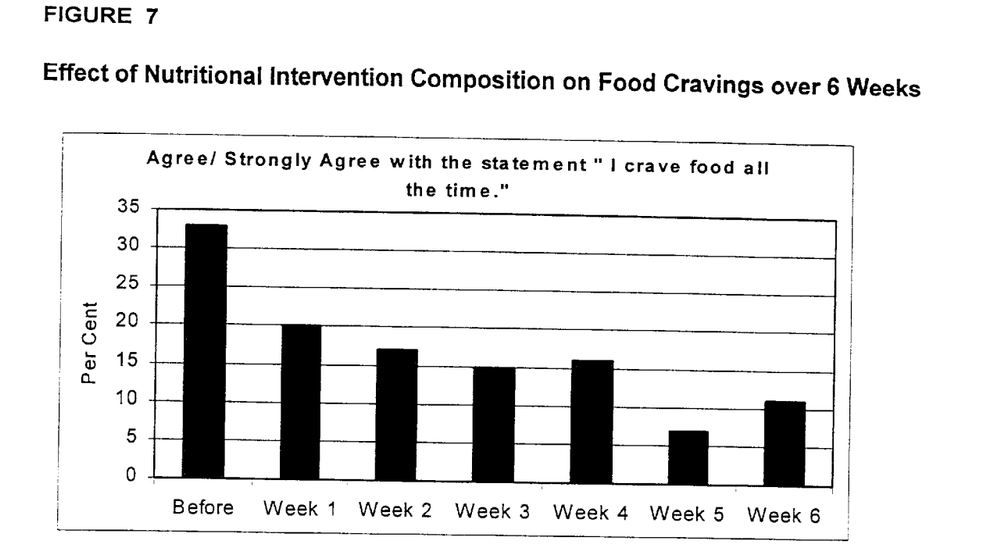
FIG. 7 is a graph showing the effect of the nutritional intervention composition on food cravings over six weeks.
Figure 8:
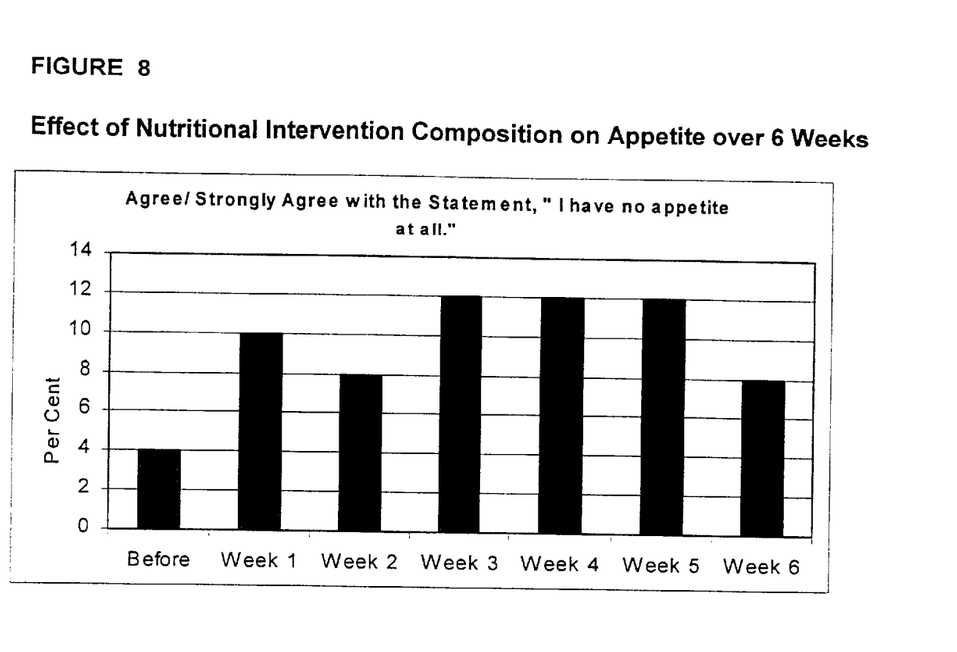
FIG. 8 is a graph showing the effect of the nutritional intervention composition on appetite over six weeks.
Figure 9:
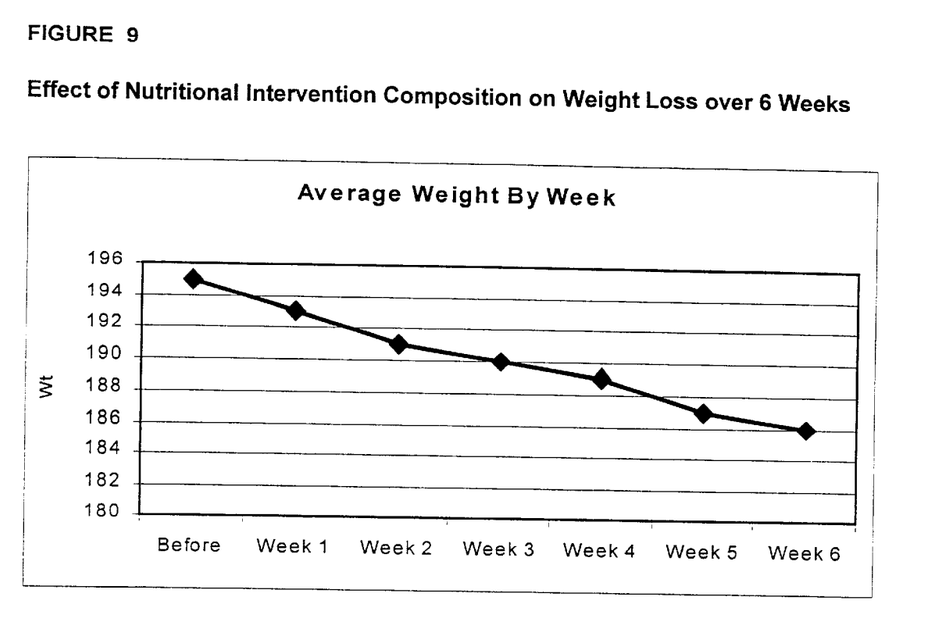
FIG. 9 is a graph showing the effect of the nutritional intervention composition on weight loss over six weeks.
Figure 10:
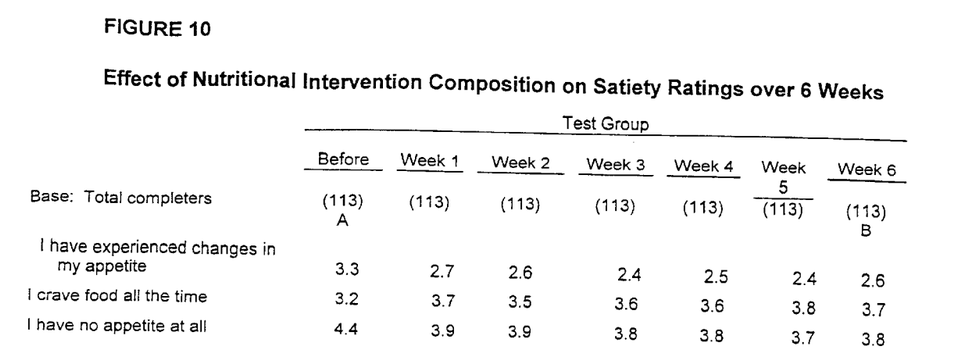
FIG. 10 is a table showing the effect of the nutritional intervention composition on mean satiety ratings over six weeks.

The invention is based on the unexpected and surprising discovery that by providing a nutritional intervention composition to stimulate CCK release and block the negative feedback mechanism of CCK release, satiety is enhanced with the consumption of fewer calories and satiation effects can be extended for up to three hours following the meal.

A second unexpected and surprising discovery is that by consuming as little as 80 calories of the nutritional composition. one can produce a significant and extended satiation effect with the consumption of a meal of only 385 calories.

A third unexpected and surprising discovery is that by combining specific soluble and insoluble fibers with plant saponins one can bind a higher percentage of the various bile acids and bile salts thereby removing a powerful inhibitor of cholecystokinin release.

The nutritional intervention composition of the invention comprises protein in the form of glycomacropeptides (GMP), fatty acids C12–C18 in length, calcium, plant saponins, soluble and insoluble fibers. The nutritional intervention composition can be taken fifteen minutes before a meal or incorporated into food to produce an extended effect on satiation.

The nutritional intervention composition is designed to achieve multiple effects leading to the increase in satiety by stimulating and maintaining levels of CCK. According to the present invention, stimulation of CCK by meals not only produces satiety but also stimulates negative feedback mechanisms, which inhibits CCK resulting in a decrease in satiety. An important aspect of the invention is that a combination of elements are used to stimulate CCK and at the same time reduce bile levels in the intestine so that CCK release is not inhibited.

Soluble fibers, including glucomannan and guar, as well as insoluble fibers, such as potato and plant saponins from alfalfa and other sources bind a greater number of bile acids and bile salts in the intestinal lumen thereby removing a powerful inhibitory factor on CCK release.

Although protein and phenylalanine are strong stimuli for CCK release, studies have shown that a casein glycomacropeptide, which is the first hydrolysis product emptied from the stomach after casein ingestion is a more potent stimulator of CCK release. Since calorie for calorie the nutritional composition of the present invention is a more potent stimulator of CCK release, it is more calorically efficient in producing satiety working through a CCK mechanism. In addition, the protein component including glycomacropeptide may also have an effect on the pancreatic feedback mechanism by serving as a substrate source for the released proteases. This may lower the amount of available proteases to inactivate CCKRP.

Calcium has been shown to stimulate CCK release through a different mechanism than the other CCK stimulating agents in this invention. Long chain fatty acids are also potent releasers of cholecystokinin. The most effective fatty acids are those between C12–C18 in length.

The present invention provides for a nutritional intervention composition in a dry powder form for enhancing satiety before a meal and extending satiety following a meal.

TABLE OF CALORIC CONTENT

| Item | gms Lower | gms Upper | Cals/gm | Cals lower | Cals upper |
|---|---|---|---|---|---|
| Protein | 1.00 | 4.00 | 4.0 | 4.00 | 16.00 |
| Carbohydrate | 0.03 | 1.00 | 4.0 | 0.12 | 4.00 |
| Long Chain Fatty Acids | 3.00 | 9.00 | 9.0 | 27.00 | 81.00 |
| Soluble and Insoluble Fibers | 1.50 | 7.00 | 0 | 0 | 0 |
| Calcium | 0.05 | 0.15 | 0 | 0 | 0 |
| Total | 5.58 | 21.15 | | 31.12 | 101.00 |

PREFERRED EMBODIMENT

| Ingredient | Source | grams | % | Range (gm) Lower | Range (gm) Upper | Percent (%) Lower | Percent (%) Upper |
|---|---|---|---|---|---|---|---|
| Protein | Casein, whey, soy | 2.81 | 17.68% | 1.00 | 4.00 | 4.23% | 38.48% |
| Glycomacropeptide | Whey Protein | 0.59 | 3.15% | 0.03 | 1.00 | 0.12% | 11.95% |
| Oleic acid | | 2.40 | 15.10% | 1.00 | 4.00 | 4.23% | 38.48% |
| Other long chain fatty acids | | 3.60 | 22.66% | 2.00 | 5.00 | 8.46% | 48.10% |
| Soluble Fiber | Guar., glucomannan, potato, sugar beet | 1.92 | 12.08% | 1.00 | 4.00 | 4.23% | 38.48% |
| Insoluble Fiber | Alfafa, cholestyramine, cellulose, potato | 1.14 | 7.17% | 0.50 | 3.00 | 2.07% | 30.32% |
| Calcium | Lactate Carbonate | 0.09 | 0.51% | 0.05 | 0.15 | 0.19% | 2.00% |
| Flavors | | 2.20 | 13.85% | 1.10 | 3.00 | 4.44% | 32.28% |
| Emulsifiers | Lecithin | 0.20 | 1.26% | 0.20 | 0.40 | 0.76% | 5.27% |
| Artificial Sweeteners | Aspartame | 0.03 | 0.19% | 0.015 | 0.60 | 0.06% | 7.52% |
| Carbohydrate | Maltodextrin | 1.00 | 6.29% | 0.50 | 1.50 | 1.95% | 17.87% |
| Totals | | 15.89 | 100.00% | 7.395 | 26.65 | | |
| Total Fatty Acids | | | | 3.00 | 9.00 | 14.53% | 67.19% |
| Total Soluble & Insoluble Fibers | | | | 1.50 | 7.00 | 7.09% | 54.28% |

ALTERNATE EMBODIMENT

| Ingredient | Source | grams | % | Range (gm) Lower | Range (gm) Upper | Percent (%) Lower | Percent (%) Upper |
|---|---|---|---|---|---|---|---|
| Protein | Casein, whey, soy | 2.81 | 22.72% | 1.00 | 4.00 | 5.56% | 46.39% |
| Glycomacropeptide | Whey Protein | 0.50 | 4.04% | 0.03 | 1.00 | 0.15% | 15.38% |
| Oleic acid | | 2.40 | 19.40% | 1.00 | 4.00 | 5.56% | 46.89% |
| Other long chain fatty acids | | 3.60 | 29.10% | 2.00 | 5.00 | 11.11% | 58.62% |
| Soluble Fiber | Guar, glucomannan, potato, sugar beet | 1.92 | 15.52% | 1.00 | 4.00 | 5.56% | 46.89% |
| Insoluble Fiber | Alfafa, cholestyramine, cellulose, potato | 1.14 | 9.22% | 0.50 | 3.00 | 2.70% | 37.36% |
| Totals | | 12.37 | 100.00% | 5.53 | 21.00 | 100.00% | 100.00% |

The nutritional intervention composition includes a flavor component for imparting a characteristic taste to the nutritional intervention composition selected from the group consisting of water soluble, natural or artificial extracts that include apple, banana, cherry, cinnamon, cranberry, grape, honeydew, honey, kiwi, lemon, lime, orange, peach, peppermint, pineapple, raspberry tangerine, watermelon, wild cherry and equivalents thereof; being in the range of 1.10 to 3.00 grams by weight of the composition.

The nutritional intervention composition may be used as a food additive added to foods selected from the group consisting of yogurt, jello, apple sauce, cottage cheese, cereal, bread, and candy bars.

The nutritional intervention composition maybe used as a food additive added to drinks selected from the group consisting of apple juice, orange juice, grape juice, grapefruit juice, cranberry juice, coffee, tea, milk, milkshakes, broth, and soup consomme Experiment One-Consumption Of the Nutritional
Intervention Composition of the Present Invention
Prior To A Meal Ten normal weight subjects (Body Mass Index=24) were administered either a placebo containing polydextrose or one containing the nutritional intervention composition of the present invention. Both the placebo and the nutritional intervention composition of the present invention were mixed with 8 oz of water. Both drinks contain 80 calories. Following consumption of either drink subjects consumed a meal consisting of 350 g (385 cal) of Stouffers macaroni and beef casserole. Two satiety tests were performed. On one occasion subjects drank 8 oz of the beverage containing the nutritional intervention composition of the present invention and the placebo beverage on the other occasion. Subjects were permitted fifteen minutes to consume their meal. Subjects rated hunger and other questions using a computer before and after drinking the beverage, before and after eating the meal and every fifteen minutes for three and one half hours after the meal. A two way repeated measure analysis of variance was used to evaluate the effect of the nutritional intervention composition of the present invention. The subjects were asked to give their ratings to the following questions:

1. How hungry do you feel right now?
2. How thirsty do you feel right now?
3. How much food would you like to eat right now?

The results showed there was no difference between the groups with regards to thirst but there was significant difference (p<0.05) with regard to hunger and how much food the subjects felt they could eat. At two hours there was a significant difference in hunger ratings and this difference continued to the end of the experiment. Similar results were seen in response to subjects' subjective ratings to the question, how much food could they eat.

Experiment Two-Addition Of the Nutritional Intervention Composition of the Present Invention to Food Ten normal weight subjects (Body Mass Index=24) were administered either a placebo yogurt containing polydextrose or the nutritional intervention composition of the present invention in low fat yogurt.

Subjects received both formulations three days apart in a crossover double blind designed protocol. Following consumption of the yogurt containing either the placebo or the nutritional intervention composition of the present invention, subjects measured hunger and thirst sensations using a visual analog scale. Measurements were taken every fifteen minutes for three and a half hours. The results showed there was no difference in thirst sensation, however there was a significant difference in hunger ratings. At 45 minutes subjects receiving a yogurt that contained the nutritional intervention composition of the present invention had significant less hunger and this decreased hunger was extended for almost two hours and ten minutes. An analysis of variance showed a significant treatment effect with a p value less than 0.05. When subjects were asked to rate "how much food they could eat" over the duration of the test there was a significant difference between subjects taking the placebo yogurt and subjects taking yogurt containing the nutritional composition of the present invention. Subjects taking the nutritional intervention composition of the present invention had a significantly less desire to eat. An analysis of variance showed a significant treatment effect with a p value less than 0.05.

Experiment Three-Effect of the Nutritional Intervention Composition of the Present Invention on weight loss and appetite over six weeks In an open trial 113 overweight subjects (Body Mass Index=27–32) between the ages of 22–55 were administered the nutrition composition of the present invention three times a day 15 minutes prior to their breakfast, lunch and dinner meals for a period of six weeks. Subjects were asked to maintain a 1740 calorie per day diet and materials were given to them to assist in their meal planning.

Each week subjects were asked to fill out a questionnaire measuring global satiety. They were asked whether they agreed or disagreed with the following statements:

1. I have experienced changes in my appetite.
2. I crave food all the time.
3. I have no appetite at all.

The results showed there was a mean weight loss of 8.82 lbs. In addition, the subjects experienced a significant change in mean satiety scores when their subjective feelings of hunger, fullness and appetite were compared to the pre-study readings.

At the end of the study 49% of the respondents Agreed/Strongly Agreed with the statement "I have experienced changes in my appetite" compared to 28% prior to the study.

At the end of the study 11% of the respondents Agreed/Strongly Agreed with the statement "I crave food all the time" compared to 33% prior to the study.

At the end of the study 8% of the respondents Agreed/Strongly Agreed with the statement "I have no appetite at all" compared to 4% prior to the study.

Respondents who lost more than 5 lbs had a greater change in mean satiety ratings over the course of the study.

The results of this open trial show that the nutritional composition of the present invention increased satiety and reduced hunger cravings in subjects that were on a calorically restricted diet. In addition the nutritional composition of the present invention produced a mean weight loss of 8.82 lbs.

ADVANTAGES OF THE PRESENT INVENTION

Accordingly an advantage of the present invention is that it provides a nutrition intervention composition for enhancing satiety before a meal.

Another advantage of the present invention is that it provides a nutrition intervention composition to extend satiety after a meal.

Another advantage of the present invention is that it provides a nutrition intervention composition that can be consumed prior to a meal to enhance satiety.

Another advantage of the present invention is to provide a nutrition intervention composition that can be added to food to extend the satiating effect of the food to which it is added.

Another advantage of the present invention is that it provides a nutrition intervention composition that it stimulates cholecystokinin release in a calorically efficient manner.

Another advantage of the present invention is that it provides a nutrition intervention composition that increases cholecystokinin by stimulating its release through a combination of nutritional agents.

Another advantage of the present invention is that it provides a nutrition intervention composition that blocks the inhibition of cholecystokinin release by binding soluble and insoluble fibers to bile acids and to bile salts.

Another advantage of the present invention is that it provides a nutrition intervention composition to cause weight loss resulting from a reduced caloric intake.

Another advantage of the present invention is that it provides a nutrition intervention composition to provide better glycemic control for Type II diabetics.

Another advantage of the present invention is that it provides a nutrition intervention composition to help Type II diabetics enhance and extend satiety in a calorically efficient fashion.

Another advantage of the present invention is that it provides a nutrition intervention composition to increase satiety in bulimics who have a defect in their normal CCK release mechanism.

Another advantage of the present invention is that it provides a nutrition intervention composition to help in the management of the bulimic patients.

Another advantage of the present invention is that it provides a nutrition intervention composition that is palatable, well tolerated and without side effects to individuals.

What is claimed is:

1. A method for enhancing and extending post meal satiety by stimulating cholecystokinin (CCK) levels in a calorically efficient manner for reducing weight comprising the step of ingesting a nutritional composition before or during a meal, wherein the nutritional composition comprises:
- a) a protein selected from the group consisting of casein, whey and soy being in the range of 1.0 to 4.0 grams by weight of said composition;
- b) a glycomacropeptide being in the range of 0.03 to 1.00 grams by weight of said composition;
- c) long chain fatty acids (C12 to C18) being in the range of 3.0 to 9.0 grams by weight of said composition;
- d) a combination of soluble fibers and insoluble fibers for binding bile acids and bile salts being in the range of 1.50 to 7.00 grams by weight of said composition; and
- e) wherein the total weight of said composition being in the range of 7.395 to 26.65 grams.

2. A method for enhancing and extending satiety by stimulating cholecystokinin (CCK) levels in a calorically efficient manner for reducing weight, in accordance with claim 1, wherein said combination of soluble fibers and insoluble fibers are selected from the group consisting of guar, glucomannan, potato, sugar beet, alfalfa and cholestyramine.

3. A method of enhancing and extending satiety by stimulating cholecystokinin (CCK) levels in a calorically efficient manner for reducing weight in accordance with claim 1, wherein said nutritional composition has a caloric content of 31.12 to 101 calories and extends satiety for at least three (3) hours following the consumption of a meal of 300 to 500 calories.

4. A method of enhancing and extending satiety by stimulating cholecystokinin (CCK) levels in a calorically efficient manner for reducing weight in accordance with claim 1, wherein said nutritional composition is in the form of a dry powder.

5. A method of enhancing and extending satiety by stimulating cholecystokinin (CCK) levels in a calorically efficient manner for reducing weight in accordance with claim 1, wherein said nutritional composition is part of a liquid drink.

6. A method of enhancing and extending satiety by stimulating cholecystokinin (CCK) levels in a calorically efficient manner for reducing weight in accordance with claim 1, wherein said nutritional composition is part of a nutritions bar.

7. A method of enhancing and extending satiety by stimulating cholecystokinin (CCK) levels in a calorically efficient manner for reducing weight in accordance with claim 1, wherein said nutritional composition is taken before a meal is consumed.

8. A method of enhancing and extending satiety by stimulating cholecystokinin (CCK) levels in a calorically efficient manner for reducing weight in accordance with claim 1, wherein said nutritional composition is taken during the consumption of a meal.

9. A method of enhancing and extending satiety by stimulating cholecystokinin (CCK) levels in a calorically efficient manner for reducing weight in accordance with claim 1, wherein said nutritional composition is a food additive.

10. A method of enhancing and extending satiety by stimulating cholecystokinin (CCK) levels in a calorically efficient manner for reducing weight in accordance with claim 9, wherein said food additive is added to a food selected from the group consisting of yogurt, gelatin, apple sauce, cottage cheese, cereal, bread, and candy bars.

11. A method of enhancing and extending satiety by stimulating cholecystokinin (CCK) levels in a calorically efficient manner for reducing weight in accordance with claim 9, wherein said food additive is added to a drink selected from the group consisting of apple juice, orange juice, grape juice, grapefruit juice, cranberry juice, coffee, tea, milk, a milkshake, broth, and soup consomme.

* * * * *